US008676333B1

(12) United States Patent
Hartman et al.

(10) Patent No.: US 8,676,333 B1
(45) Date of Patent: Mar. 18, 2014

(54) APPARATUS AND METHODS FOR PROVIDING ELECTRICAL STIMULATION

(71) Applicants: Eric C. Hartman, Nicholasville, KY (US); John D. Alton, Lexington, KY (US); Tarik S. Aweimrin, Lexington, KY (US); Jesse R. Smith, Frankfort, KY (US); Lee Gentry Barnett, Lexington, KY (US); Natalie L. Hatfield, Lexington, KY (US)

(72) Inventors: Eric C. Hartman, Nicholasville, KY (US); John D. Alton, Lexington, KY (US); Tarik S. Aweimrin, Lexington, KY (US); Jesse R. Smith, Frankfort, KY (US); Lee Gentry Barnett, Lexington, KY (US); Natalie L. Hatfield, Lexington, KY (US)

(73) Assignee: CustomKYnetics, Inc., Versailles, KY (US)

( * ) Notice: Subject to any disclaimer, the term of this patent is extended or adjusted under 35 U.S.C. 154(b) by 0 days.

(21) Appl. No.: 13/621,453

(22) Filed: Sep. 17, 2012

Related U.S. Application Data

(63) Continuation-in-part of application No. 12/826,073, filed on Jun. 29, 2010, now Pat. No. 8,271,090.

(60) Provisional application No. 61/222,738, filed on Jul. 2, 2009.

(51) Int. Cl.
*A61N 1/00* (2006.01)

(52) U.S. Cl.
USPC .............................................. 607/48

(58) Field of Classification Search
USPC ............................................ 607/48
See application file for complete search history.

(56) References Cited

U.S. PATENT DOCUMENTS

| 4,919,418 A * | 4/1990 | Miller ........................... 482/6 |
| 2005/0197680 A1* | 9/2005 | DelMain et al. .............. 607/60 |
| 2011/0029042 A1* | 2/2011 | Malinowski et al. ......... 607/59 |

* cited by examiner

*Primary Examiner* — Robert N Wieland
(74) *Attorney, Agent, or Firm* — King & Schickli, PLLC

(57) ABSTRACT

An apparatus is disclosed for providing a single-channel, interlaced electrical stimulation signal to a subject from a stimulation unit using a transmission line and a plurality of electrodes. The apparatus may include one or more discrete nodes, each adapted for receiving the electrical stimulation connecting with at least one pair of the plurality of electrodes. The node or nodes are adapted to select the particular signal intended for the electrodes associated with that node. The apparatus may also include one or more sensors in communication with the stimulation unit for communicating information relevant to the subject being stimulated.

23 Claims, 17 Drawing Sheets

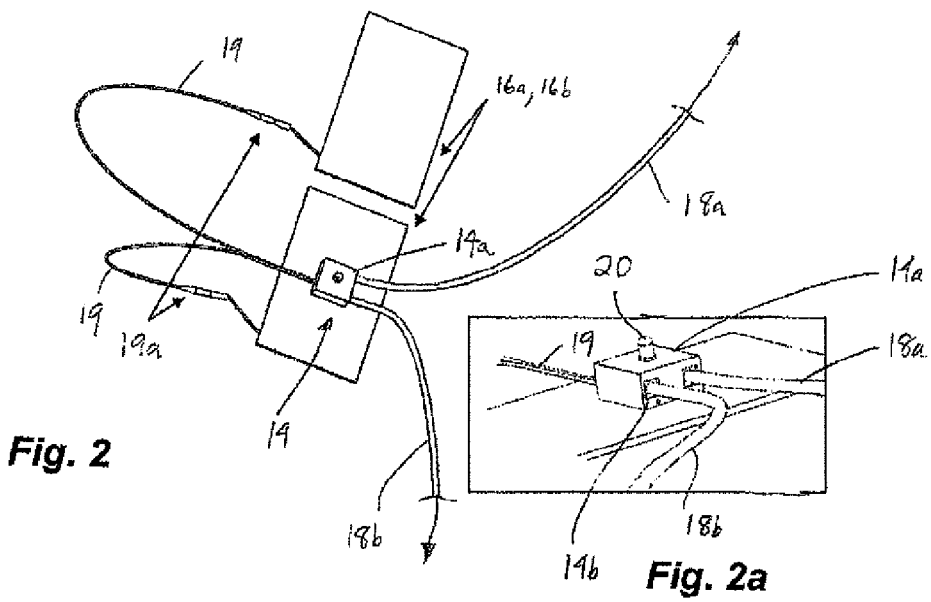
Fig. 2
Fig. 2a
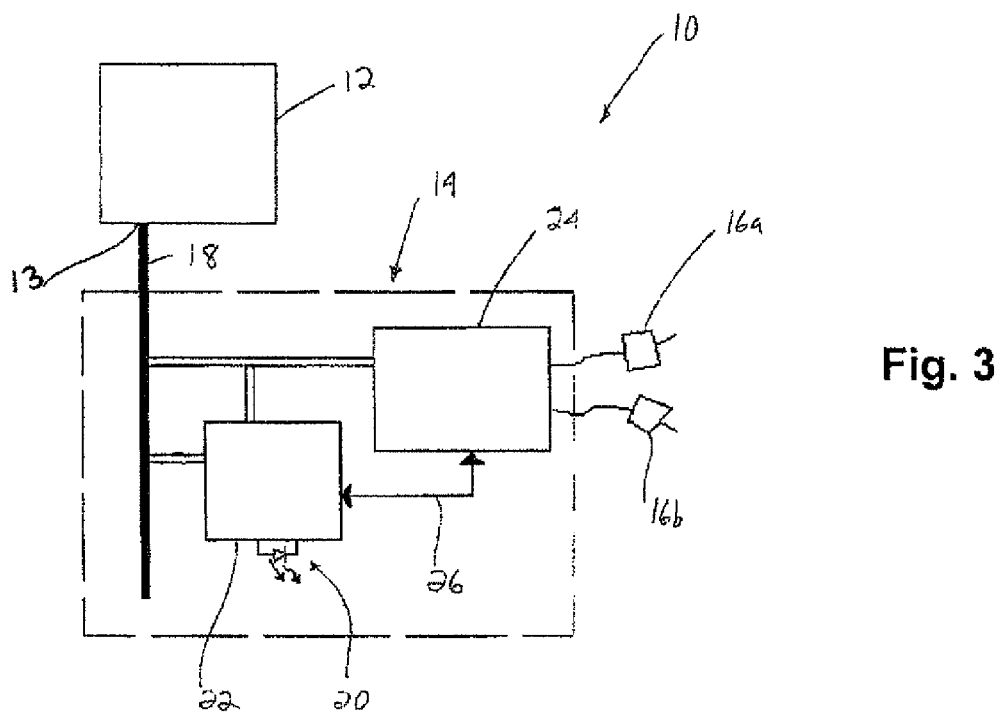
Fig. 3

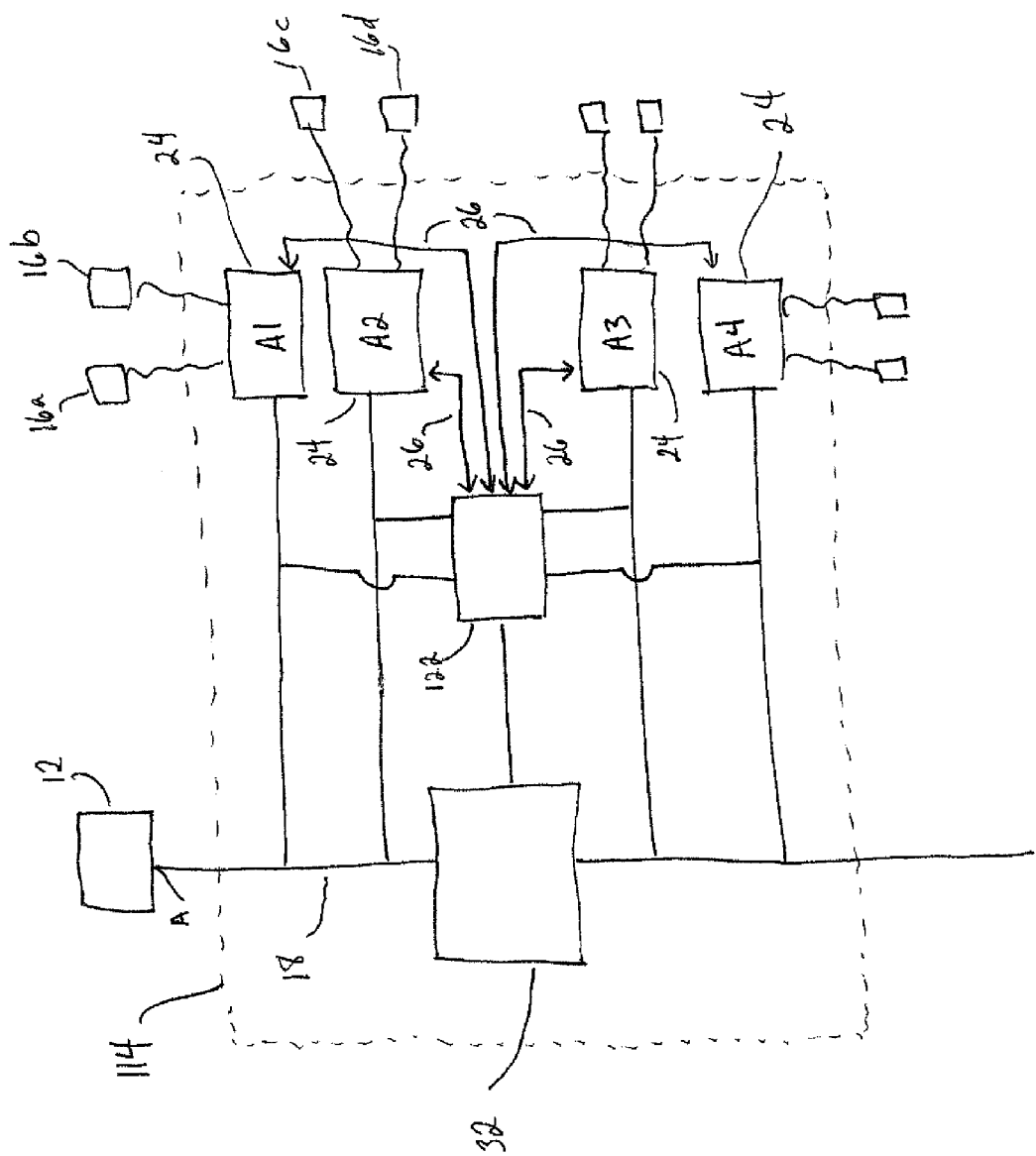

APPARATUS AND METHODS FOR PROVIDING ELECTRICAL STIMULATION

This application is a Continuation-in-Part of U.S. patent application Ser. No. 12/826,073, filed Jun. 29, 2010, now U.S. Pat. No. 8,271,090, issued Sep. 18, 2012, which claims the benefit of U.S. Provisional Patent Application Ser. No. 61/222,738, filed Jul. 2, 2009, the disclosures of which are incorporated herein by reference.

STATEMENT OF GOVERNMENT SUPPORT

This invention was supported by two grants from the National Institute of Health, Department of Health and Human Services under contract numbers R43HD062065 and R44HD062065. The government may have certain rights in this invention.

COPYRIGHT STATEMENT

A portion of the disclosure of this document contains material subject to copyright protection. No objection is made to the facsimile reproduction of the patent document or this disclosure as it appears in the Patent and Trademark Office files or records, but any and all rights in the copyright(s) are otherwise reserved.

TECHNICAL FIELD

The present disclosure relates to the physical therapy arts and, more particularly, to apparatus and methods for providing therapy with electrical stimulation and related methods.

BACKGROUND OF THE INVENTION

Various types of physical therapy, including rehabilitative exercise, may employ externally applied, transcutaneous stimulation in the course of treating a subject. Typically, the stimulation comprises discrete electrical pulses generated by an external stimulator, and travel through associated wires to one or more electrode pairs placed on the skin adjacent a target location. In the case of exercise therapy, the electricity passing through the skin causes the targeted muscle fibers to activate or contract, even without voluntary control by the subject. Accordingly, such stimulation is frequently used in situations where the subject is incapacitated or otherwise unable to control function of the muscles, such as in the event of an injury to the brain or associated portion of the nervous system.

Despite the past use of electrical stimulation for providing therapy, certain limitations in the application of this technology and the results produced remain. For one, a pair of electrodes is typically associated with a single stimulation channel providing the electrical pulses to the targeted location. Thus, to simultaneously or even sequentially provide stimulation to different muscle groups or otherwise in a distributed fashion, pairs of electrodes must each be connected to a different channel of a stimulation source using individual wire for transmitting the pulses. Thus, for example, to stimulate three different muscle groups, three pairs of electrodes would be used, with each pair having an individual wire for transmitting the stimulation pulses from a three channel stimulator (and, to make the wires universal, they are typically made longer than necessary to reach a given body part). Aside from greatly increasing the cost and complexity, such wires may easily become tangled or damaged during the exercise movement.

In typical applications, the stimulation pulses delivered from the source are also infinitesimally small compared to the inter-pulse interval. For example, a given pulse may be active for less than 1,000 microseconds for every 20,000 microseconds of time that passes. Thus, there is a substantial amount of unused potential of the stimulation device while it waits to deliver the next pulse.

Accordingly, a need is identified for apparatus and methods that provide an improvement in delivering electrical stimulation to a subject in an efficient and effective manner. In particular, the apparatus would use a single transmission line per channel connected to serially arranged nodes, each associated with an electrode pair, to minimize the number of wires required. This would potentially allow for the application of stimulation to an unprecedented number of electrodes without significantly adding to the complexity or cost. Moreover, the apparatus would be capable of maximizing the potential of the stimulation device, which further enhances efficiency and reduces cost. Overall, a significant improvement over known past approaches would be realized.

SUMMARY OF THE INVENTION

One aspect of the disclosure is an apparatus for providing electrical stimulation to at least one subject using at least one transmission line and a plurality of pairs of electrodes. The apparatus comprises a stimulation unit for producing a single-channel interlaced output signal comprising a plurality of stimulation pulses, wherein said output signal is configured for selective delivery to the subject via at least one pair of electrodes.

In one embodiment, at least one first stimulation pulse is configured to stimulate a first subject, and a second stimulation pulse is configured to stimulate a second subject.

In another embodiment, the apparatus further includes at least one node for selecting a first stimulation pulse configured for delivery to a first pair of electrodes associated with the node. The node may be further configured for independently selecting a second stimulation pulse which is configured for delivery to a second pair of electrodes associated with the node.

The apparatus may further include a plurality of nodes, each node adapted for selecting at least one stimulation pulse intended for at least one pair of electrodes associated with said node.

In a further embodiment, the stimulation unit is adapted for simultaneous use with a first piece of exercise equipment and a second piece of exercise equipment. The stimulation unit may also be adapted for simultaneous use with a first subject and a second subject. In another aspect, the stimulation unit may be adapted for simultaneously stimulating a first portion of the subject's body using at least one first node associated with a first pair of electrodes and a second portion of the subject's body using at least one second node associated with a second pair of electrodes. In a further aspect, the stimulation unit may be adapted for simultaneously stimulating the subject using at least one first node associated with at least two pairs of electrodes, each for stimulating a different portion of the subject's body.

In an additional embodiment, the stimulation unit may include a plurality of ports, each for delivering the single-channel interlaced output signal.

A further aspect of the disclosure relates to an apparatus for providing an electrical stimulation in the form of a plurality of interlaced stimulation pulses through at least one transmission line, wherein a first stimulation pulse is intended for a first pair of electrodes for delivering said stimulation pulse to an external skin surface of a subject. The apparatus comprises at least one node adapted to connect to the transmission line for receiving the plurality of stimulation pulses, said node adapted for selecting and delivering a first stimulation pulse intended for the first pair of electrodes.

Preferably, the node includes a first connector for connecting to the first pair of electrodes. The node may further include a plurality of connectors, each for connecting to one of a plurality of pairs of electrodes.

In one embodiment of the invention, the node is further adapted for selecting and delivering a second stimulation pulse intended for a second pair of electrodes associated with the node.

In another embodiment, the apparatus additionally includes a sensor for sensing a condition of the subject and communicating the condition to the stimulation unit. In one aspect, the sensor may be connected to the node.

In another embodiment, the apparatus may further include a stimulation unit for generating the output stimulation via a single channel. The stimulation unit may include a plurality of ports for distributing the single-channel output stimulation to the at least one node.

An additional aspect of the disclosure relates to an apparatus for stimulating a subject via at least one first pair of electrodes. The apparatus comprises a stimulation unit for producing a single-channel interlaced output signal comprising a plurality of stimulation pulses, wherein at least one first pulse is intended for the first pair of electrodes. In addition, the apparatus includes at least one node for receiving the plurality of stimulation pulses and for selecting and delivering the first pulse to the first pair of electrodes.

In one embodiment, the apparatus may further include a sensor for sensing a condition of the subject and for communicating information regarding the condition to the stimulation unit.

In another aspect of the disclosure, the invention relates to an exercise device for use with the apparatus described herein.

BRIEF DESCRIPTION OF THE DRAWING FIGURES

FIG. 2 illustrates a single stimulation node according to one aspect of the disclosure;

FIG. 2a is a close-up view of the stimulation node of FIG. 2;

FIG. 3 is a schematic diagram illustrating the details of a circuit included in one embodiment of a stimulation node;

FIG. 7 is a schematic diagram illustrating the details of a circuit included in another embodiment of a stimulation node;

Figure 13:
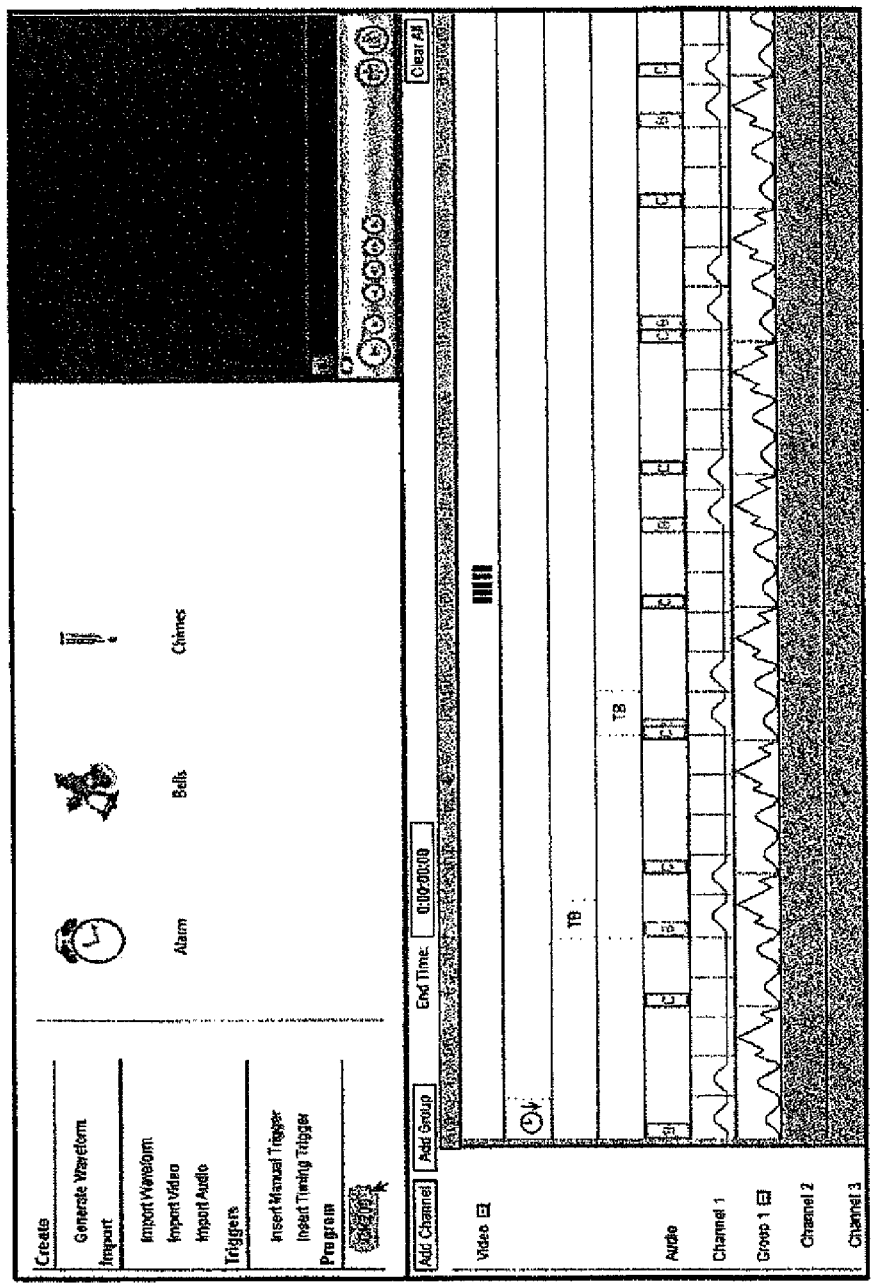
Figure 14:
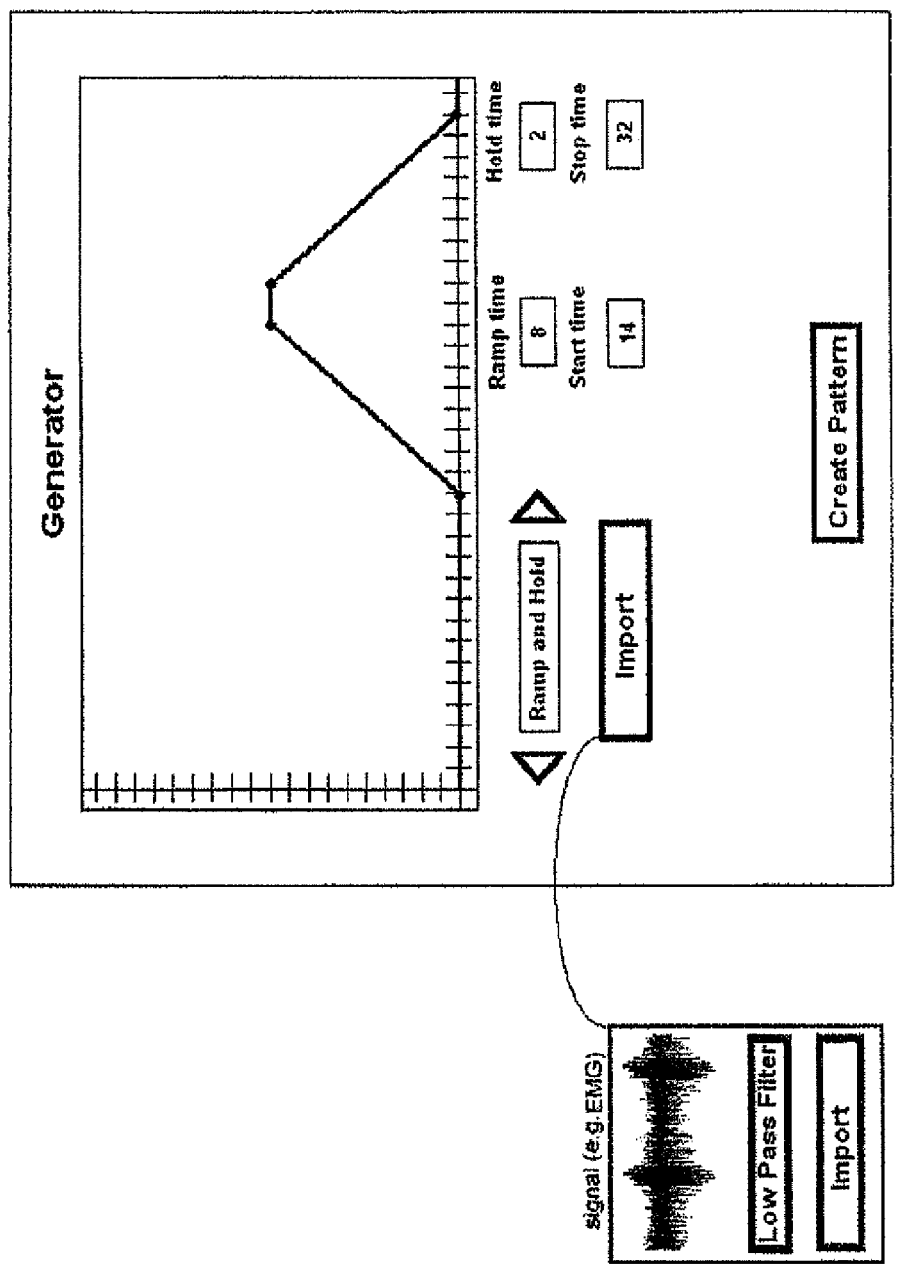
Figure 15:
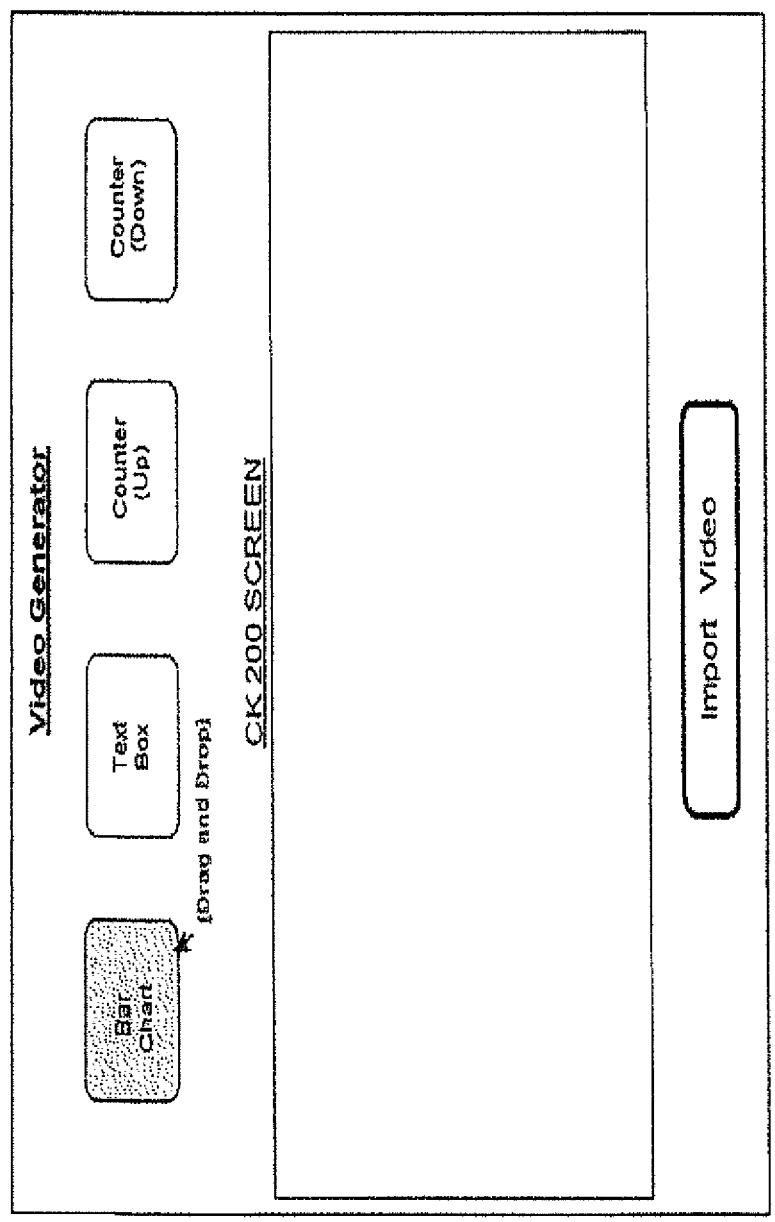
Figure 16A:
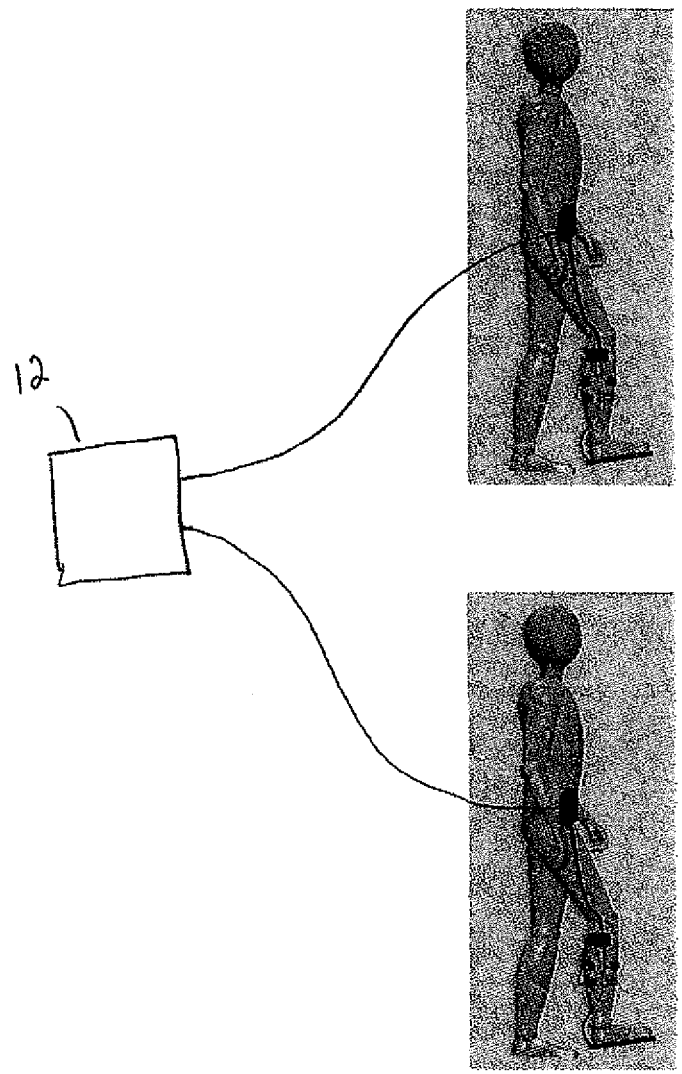
Figure 16B:
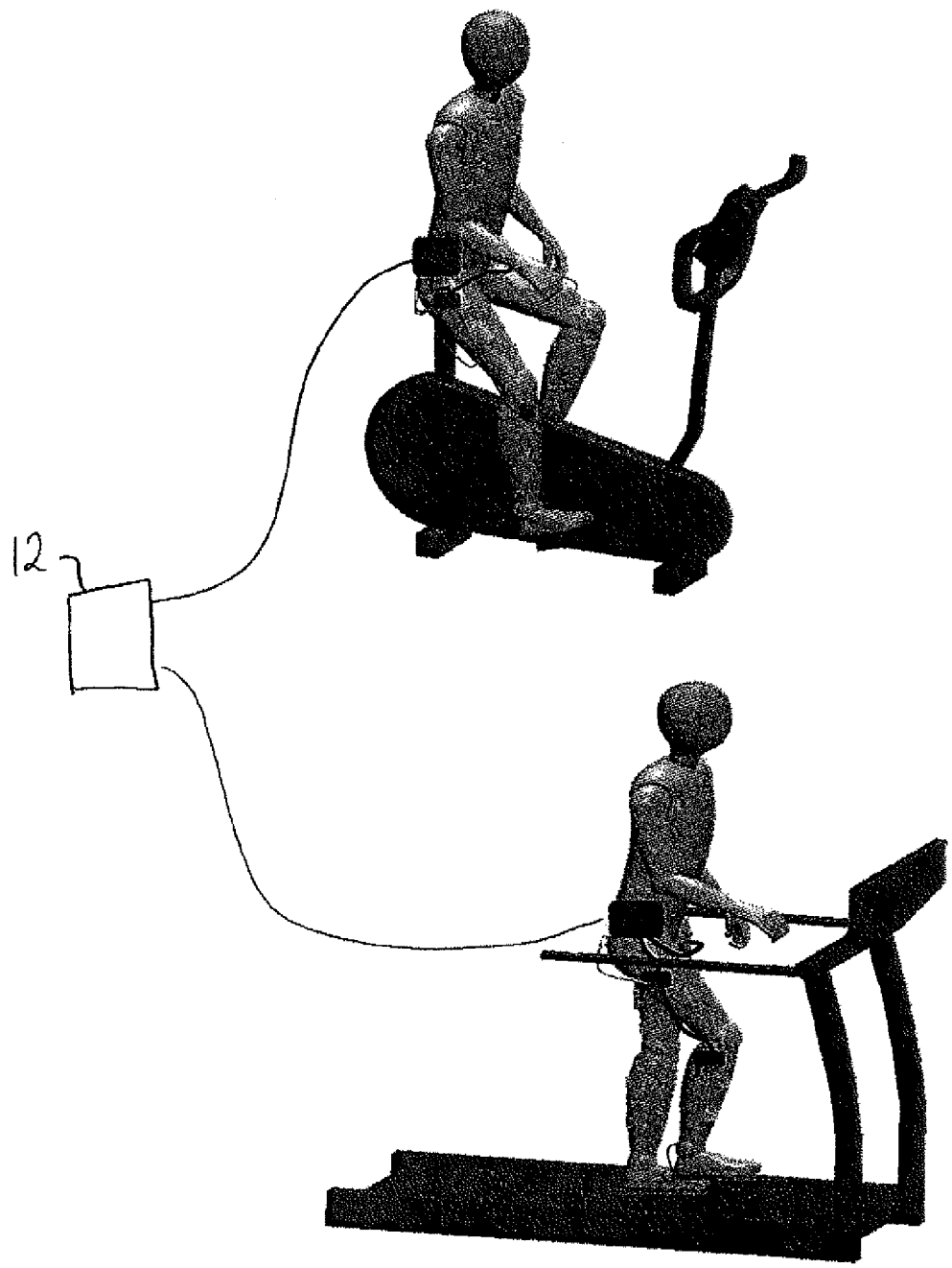

FIGS. 13-15 comprise screen shots from software programs that may be used for programming the system; and FIGS. 16a and 16b illustrate the use of one embodiment of the system in an exercise environment.

DETAILED DESCRIPTION OF THE INVENTION

One embodiment relates to an active distributed electrode array (ADEA) system 10 for electrical stimulation therapy and, neuromuscular electrical stimulation, in particular. The system 10 includes a stimulation unit 12 having at least one output that, using other components described herein, may be shared to provide essentially an unlimited number of virtual stimulation channels with intelligently controlled coordinated simulation patterns. This allows for use in high channel count applications without the added cost and complexity of a rigidly defined high channel count NMES unit. The system 10 further allows virtual stimulation channels to be added and/or removed as needed by the therapist to form a low-cost network of stimulation nodes using a minimal set of wires and simulation that is controlled automatically by the stimulation unit 12.

The stimulation unit 12 may be adapted to output a single-channel interlaced output signal which includes a plurality of stimulation pulses. The output signal may be configured for selective stimulation of at least one first pair of electrodes 16a, 16b, independent of any other electrodes. The plurality of stimulation pulses may be configured such that a single pulse is intended for a single electrode pair.

Figure 1A:
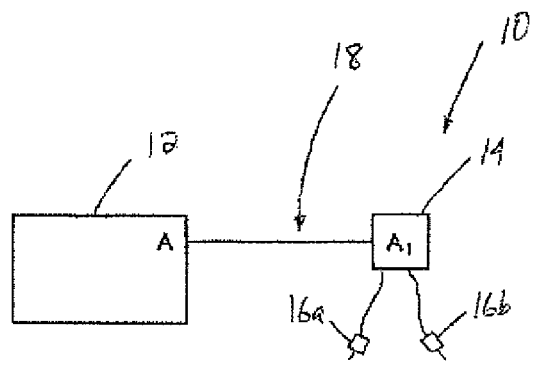
FIGS. 1a-1d illustrate schematic diagrams of various configurations of the stimulation system in accordance with the principles disclosed herein.

In one embodiment, as shown in FIG. 1a, the stimulation unit 12 may be used in connection with a single node 14 (i.e. virtual channel) via a transmission line 18. The node 14 may be associated with one pair of electrodes 16a, 16b for applying stimulation to a particular location, such as the skin surface adjacent a muscle or muscle group of a human subject in need of therapy (e.g., assisted exercise or rehabilitation, including possibly pain management). Preferably, the node 14 is "intelligent," such that it is adapted for selecting the individual pulse or pulses from the output signal which are intended for the electrode pair 16a, 16b associated with that node. In such an embodiment, the pulses from the output signal which are not intended for the electrode pair 16a, 16b associated with that node 14 would not pass to said electrodes. The "intelligence" of the node is discussed in further detail below.

Figure 1B:
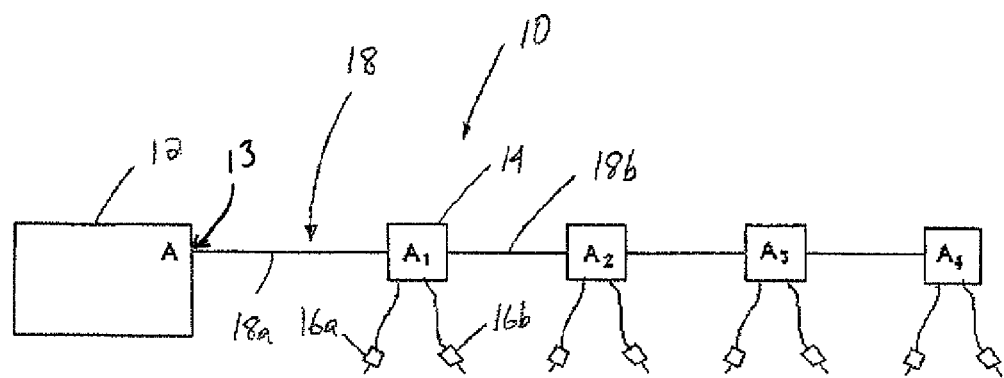

As shown in FIG. 1b, the stimulation unit 12 may further be adapted to output stimulation pulses to a plurality of discrete stimulation nodes 14 (i.e., virtual channels A1-A4) associated with each output channel, rather than to a single electrode pair. Each node 14, is in turn, associated with a pair of electrodes 16a, 16b. Additionally, each node 14 is adapted for selecting the individual pulse or pulses from the output signal which are specifically intended for the electrodes 16a, 16b associated with that node. As illustrated, these electrodes 16a, 16b may be discrete and thus comprise separate flat pads of a flexible material, and may be associated with suitable fasteners (adhesives, straps, bands, etc., not shown) for attachment to the skin surface. Four nodes 14 are shown in FIG. 1b for purposes of illustration, but is should be appreciated that any number could be used. In the illustrated embodiment, the node 14 is connected to a surface of the electrode pad opposite the surface for applying the stimulation to the skin surface of the subject, but it should be appreciated that the node could be a separate structure as well.

The nodes 14 may be connected together and to the stimulation unit 12 using transmission line 18, which may comprise multiple wires and thus be adapted to provide not only the simulation pulses, but also communication signals. In the illustrated embodiment, the connection is made in a daisy-chain fashion, such that a single transmission line 18 connects the stimulation unit 12 to each successive node 14 in the chain. Thus, for example, FIG. 2 shows that the line 18 includes a first segment 18a for connecting the node 14 with the stimulation unit 12, and a second segment 18b for connecting to the next successive node (e.g., A2, if node 14 in FIG. 2 is A1).

As should be appreciated, segments of transmission line 18 may be added for connecting additional nodes 14 to the array. Regardless of the number of segments or precise form used, the use of a single, external transmission line 18 from the stimulation unit 12 to the nodes 14 associated with a particular channel may be advantageous because the number of wires that must be managed is greatly reduced (usually, two per channel). This not only greatly simplifies the set up process, but also reduces the potential for damage as the result of the exercise movement.

The stimulation unit 12 may further include a plurality of ports 13 for transmitting the same single-channel interlaced output signal through each port 13 simultaneously. Such a configuration may be achieved by splitting the single-channel signal into a plurality of branches within a housing surrounding the stimulation unit. Each branch of the signal may be associated with an individual port 13 in the housing.

Figure 1C:
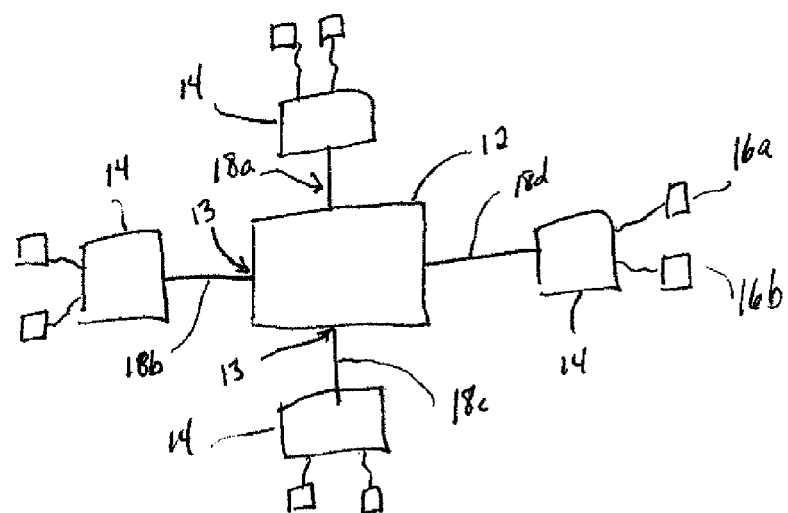
Figure 1D:
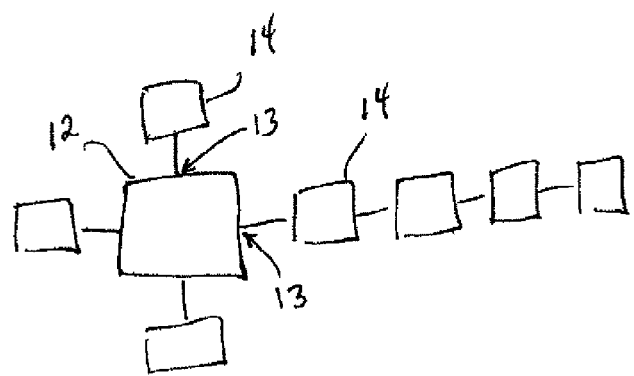

This embodiment may allow the system 10 to achieve a modular effect allowing for a variety of configurations. For example, FIG. 1c illustrates a star configuration in which the stimulation unit 12 includes four branches 18a-18d of the single-channel output, each of which is adapted to transmit the signal to a distinct node 14. In another embodiment illustrated in FIG. 1d, the system 10 may assume a hybrid configuration including certain branches of the signal transmitting stimulation output to a single node 14, while another branch may transmit the stimulation output to a daisy-chain of nodes 14.

Referring to the block diagram in FIG. 3, the node 14 is shown as being connected to a simulation unit 12 via transmission line 18 which is connected to a port 13. Through this transmission line 18, the stimulation unit 12 may transmit the single-channel interlaced stimulation signal which may correspond to one or more virtual channels. For example, in the embodiment of FIG. 1b, channel A would correspond to virtual channels A1-A4. Port 13 may provide the node(s) 14 with power, communication, and access to the stimulation output channel of the unit 12. In one embodiment, there are two stimulation channels A and B, each delivered through different ports 13 to distinct arrays of discrete nodes 14 arranged in tandem (see FIGS. 7 and 8), but more or fewer may be used depending on the particular application.

The connection of the transmission line 18 or the segments 18a, 18b thereof to the node 14 is made in a releasable fashion. For example, in FIGS. 2 and 2a, the node 14 comprises a housing 14a (which is optional), and releasability is achieved using suitable receptacles 14b on the housing 14a. These receptacles 14b may take the form of a conventional telephone (RJ-11) jack, for associating with suitable connectors on the corresponding ends of the segments 18a, 18b. By using common connectors releasably attached in this manner, the nodes 14 may be added or removed along the transmission line 18 with ease.

Suitable lines 19 also connect each node 14 to the electrodes 16a, 16b for providing the stimulation pulses. This connection may also be established using releasable connectors 19a (e.g., pins for positioning in jacks associated with pigtail leads) to allow for the removal and replacement of the electrodes 16a, 16b, if necessary or desired. The node 14 is shown in FIGS. 2 and 2a as being carried by one of the electrodes 16a, 16b in the pair, but this is entirely optional. Each node 14 may also associate with an indicator 20 for providing a signal indicating an active condition (i.e., the stimulation current is reaching the node and/or flowing to the electrodes 16a, 16b), as well as possibly indicating the stimulation intensity (e.g., as a function of current).

At least one, and preferably all of the nodes 14 are "intelligent" and thus may be adapted to receive and process the stimulation pulses received from the stimulation unit 12. For example, the node 14 may include a controller for processing and selectively outputting the stimulation pulses intended only for an electrode pair 16a, 16b for a particular operation (e.g., stimulating a muscle group), while blocking pulses intended for the other electrodes/muscle groups. To achieve this goal, each node 14 may include a pulse selection circuit 22 and a pulse gating circuit 24, which work together to provide certain predetermined operating modes.

The pulse gating circuit 24 serves as the interface between the stimulation unit 12 and the electrodes 16a, 16b connected to each node 14. In a pass-through mode, the gating circuit 24 allows stimulation pulses from the unit 12 to pass to the subject donning the electrodes. In blocking mode, the gating circuit 24 blocks pulses intended for other nodes 14.

The pulse selection circuit 22 in turn is responsible for communicating with the stimulator 12, monitoring the stimulation pulse train on a pulse-by-pulse basis, enabling the pulse gating circuit (such as via an enable line 26), indicating node activity (such as via the stimulation indicator 20, which is shown in FIG. 3 as comprising a light-emitting diode), and allowing for the selection of a particular virtual channel via a selector switch (not shown). A suitable controller associated with each node 14 may be used to perform these functions, or alternatively an application specific integrated circuit (ASIC) may be used.

Figures 4, 5:
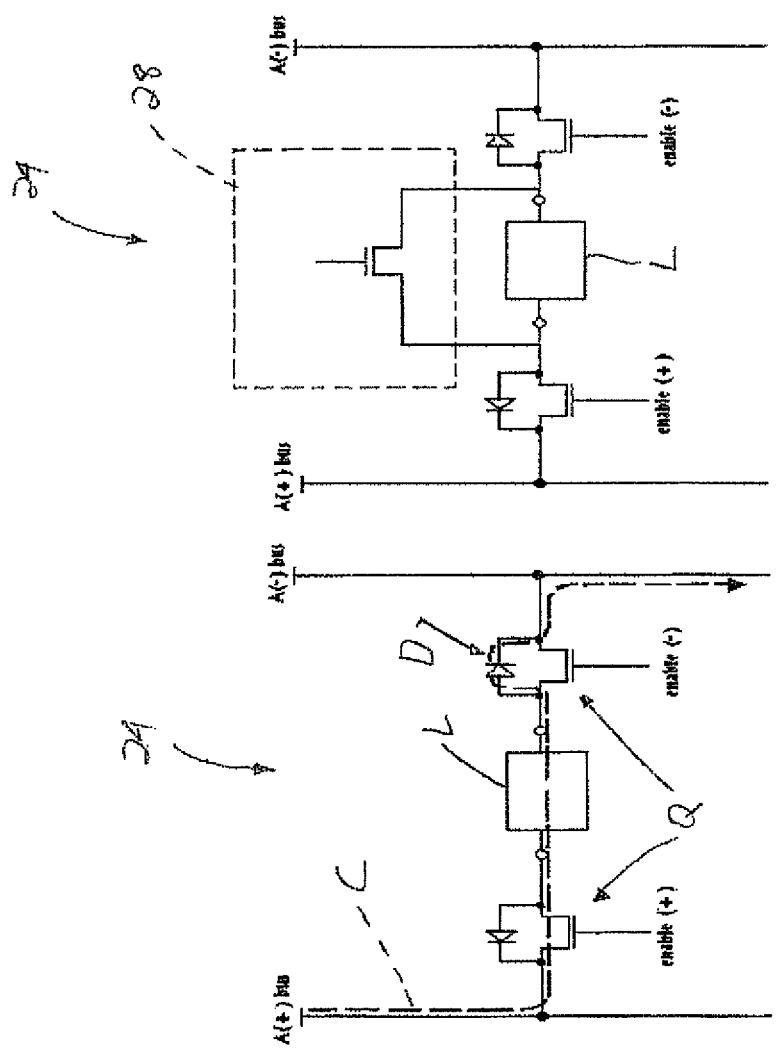
FIGS. 4 and 5 are circuit diagrams showing alternate approaches to a pulse gating circuit that may form part of a stimulation node.

The pulse gating circuit 24 may comprise a discrete transistor-based circuit or a TRIAC, but other arrangements may be possible as well. For example, FIGS. 4 and 5 present schematic diagram for two possible alternative applications for forming the pulse gating circuit 24 for each stimulation node 14 of the system 10. The block L represents the load (i.e., the electrodes 16a, 16b connected by tissue), and transistors Q control current flow through the load L when the stimulation unit 12 generates a pulse on the "A" stimulation bus. Current flow (shown as dashed line C in this example) proceeds from the A(+) stimulation output through the transistor Q, load L, and diode D before returning to the unit 12 via the A (−) bus. This flow may be reversed to pass the second phase when two events occur: (1) the pulse selection circuit 22 withdraws the enable (+) line and asserts the enable (−) line, and (2) the stimulator 12 switches the polarity of the A(+) and A(−) bus in preparation for generating the second phase of the stimulation pulse.

In FIG. 5, the shunt circuit 28 comprises an extra transistor that is placed in parallel with the electrodes (i.e., load L). This circuit 28 is intended to prevent an unintended muscle contraction caused by leakage current through the gating circuit 24 (i.e., a pulse that is not fully blocked when the gating circuit is disabled). This provides a path for the leakage current to flow that bypasses the electrodes. The transistor of shunt circuit 26 would be enabled whenever both legs of the gating circuit 24 are disabled. Alternatively, two relays (not shown) could be used in place of transistors Q in FIG. 4. The relay coil would be excited by the pulse selection circuit 22.

Figure 6:
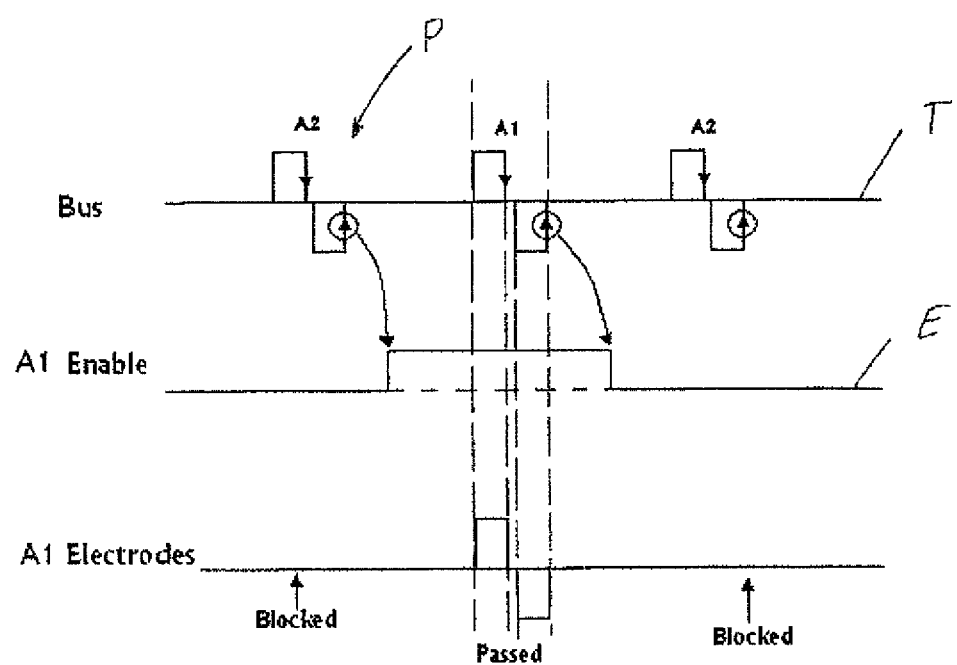
FIG. 6 is a timing diagram showing the possible operation of the pulse gating circuit to control the delivery of stimulation pulses to the electrodes associated with a particular node.

A timing diagram illustrating one possible embodiment of the monitoring and triggering tasks of the pulse selection circuit 22 is shown in FIG. 6. Pulses P of the interlaced pulse train T are shown for virtual channels A1 and A2. Trigger events are shown on the falling edges of each stimulation pulse P, and may cause a microcontroller interrupt, such that the interrupt service routine determines if the output of the pulse gate circuit 24 of a particular node 14 should be enabled (such as by counting the pulses and enabling for pulses which are intended to be output using the particular electrodes 16a, 16b). To enable a pulse P to the particular virtual channel, the enable signal E may be set high during the inter-pulse interval before the pulse to be output and return to the disabled state during the inter-pulse interval following the desired pulse output. The output to the A1 electrodes 16a, 16b are shown, indicating that the A1 pulse passes and the A2 pulses are blocked.

Alternative arrangements may also be used to control the gating circuit 24. For instance, a microcontroller associated with each node 14 could use an error-checking scheme to determine the inter-phase interval (i.e., the period between anodic and cathodic pulses for the same channel) from the inter-pulse interval (i.e., the period between successive pulses for different channels), and then disable the node if an error is detected. Alternative approaches could be the use of pulse width to evaluate which pulses should be outputted using the electrodes associated with a node 14, or an asynchronous clocking scheme in which the nodes and stimulation unit 12 employ synchronized clock rates to output pulses during a particular window of time. Yet another alternative approach could be for the controller (stimulation unit 12) to send a command during the interpulse interval to enable the desired channel prior to outputting a pulse.

In another embodiment as shown in FIG. 7, the stimulation unit 12 is designed to transmit stimulation output to a node 114 associated with a plurality of pairs of electrodes 16a, 16b. Preferably, the node 114 is an "intelligent" node, and is thus adapted to receive and process the stimulation pulses received from the stimulation unit 12. For example, the nodes 114 may process and selectively output to a first pair of electrodes 16a, 16b, the stimulation pulses intended only that first electrode pair 16a, 16b for a particular operation (e.g., stimulating a muscle group), while blocking pulses intended for a second electrode pair 16c, 16d. This selection may be accomplished by the interaction of one or more pulse selection circuits 122 and a plurality of pulse gating circuits 24, as described above. In the embodiment including a single pulse selection circuit 122, the node may further include a plurality of selector switches (not shown), such as one selector switch associated with each gating circuit.

As illustrated in FIG. 7, the node 114 may further include a bus controller 32 for interfacing between the transmission line 18 and the other elements of the node. For example, the bus controller 32 may identify and/or verify the particular node 114 to the stimulation unit 12, and may receive and process the stimulation pulses from the stimulation unit 12 in order to determine which pulses are intended for the electrodes associated with that node 114. Those pulses intended for the electrodes of that node may be passed to the other elements within the node 114, while those pulses not intended for the electrodes of that node may be blocked. The bus controller 32 may further be configured to instruct the stimulation unit 12 which of the plurality of electrode pairs 16a, 16b are connected to the node 114.

As may be understood from the modular nature of the system, one or more nodes 14 associated with a single pair of electrodes may be used in combination with one or more nodes 114 associated with a plurality of pairs of electrodes.

Figure 8A:
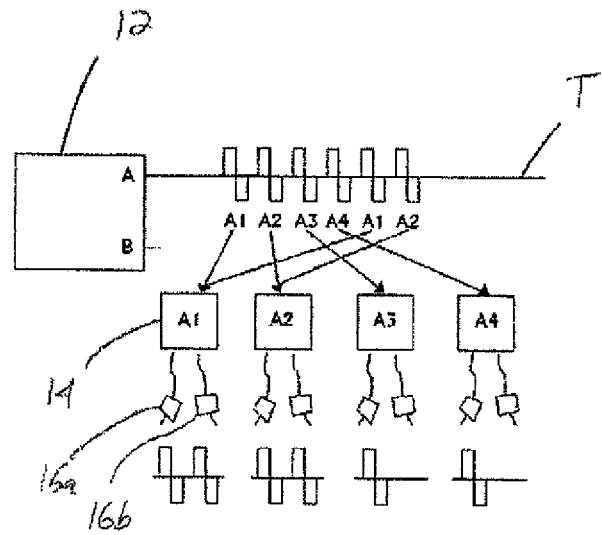
FIG. 8a illustrates a first mode of operation of the system in accordance with a first embodiment of a series of nodes.

In any case, the system 10 may be configured to operate in two possible modes: (i) pulse sharing; and (ii) channel phasing. In pulse sharing mode, the unit will configure a plurality of virtual channels (e.g., A1-A4) to be active and then output an interlaced pulse train T of stimulation provided by stimulation unit 12 in which every $i^{th}$ pulse is intended for the $i^{th}$ node 14. Thus, as shown in FIG. 8a, the nodes 14 will parse the pulse train T to selectively output only the pulses intended for the particular node 14 (i.e., output every $4^{th}$ pulse). In this mode, the stimulation unit 12 may be used to simultaneously activate multiple muscle groups using a single channel and thus form a distributed array.

Figure 8B:
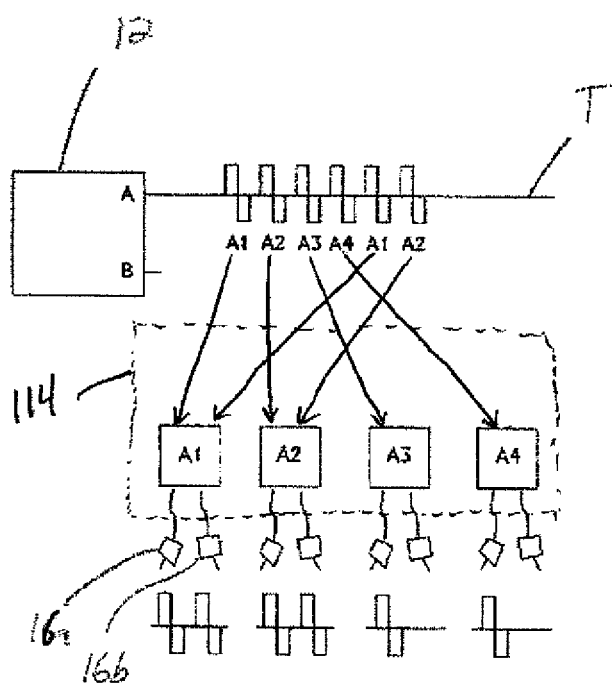
FIG. 8b illustrates the first mode of operation of the system in accordance with another embodiment of a stimulation node.

In the embodiment of a node 114 associated with a plurality of electrode pairs in pulse sharing mode, the plurality of virtual channels (e.g., A1-A4) may all be associated with the single node 114. As above, the stimulation unit 12 may provide an interlaced pulse train T of stimulation in which every $i^{th}$ pulse is intended for the $i^{th}$ virtual channel. As shown in FIG. 8b, each electrode pair represents a particular virtual channel. The single node 114 may parse the pulse train T to selectively output only the pulses intended for a particular virtual channel (e.g. A1) to that virtual channel within the node 114. The remaining pulses may be directed to a different virtual channel (e.g. A2-A4) within the node 114, or may be blocked if the pulse is not intended for a virtual channel within that node. In this embodiment, the stimulation unit 12 and a single node 114 may be used to simultaneously activate multiple muscle groups using a single channel.

Figure 9A:
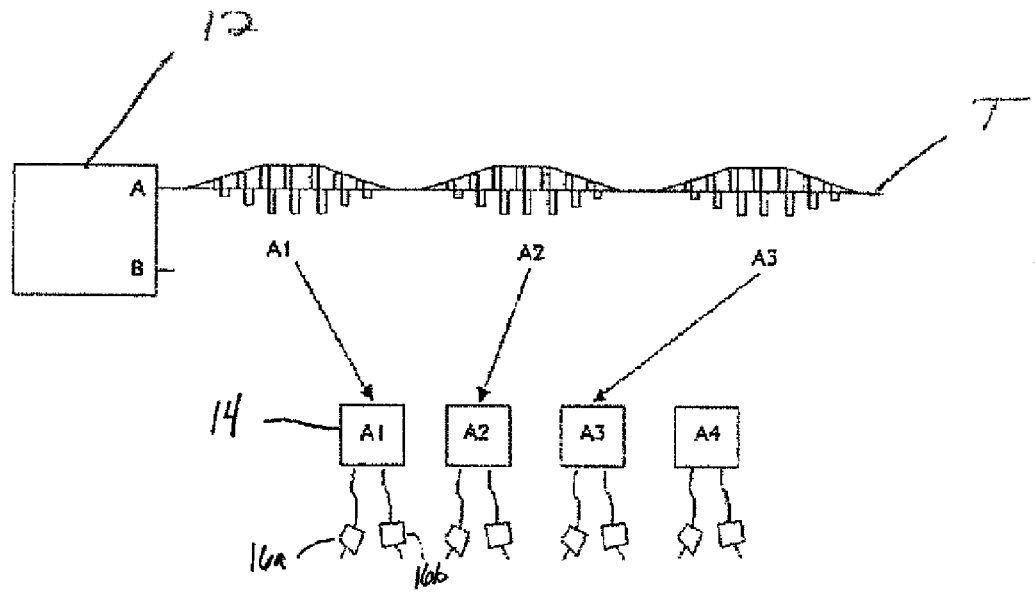
FIG. 9a illustrates a second mode of operation of the system in accordance with the first embodiment of a series of nodes.
Figure 9B:
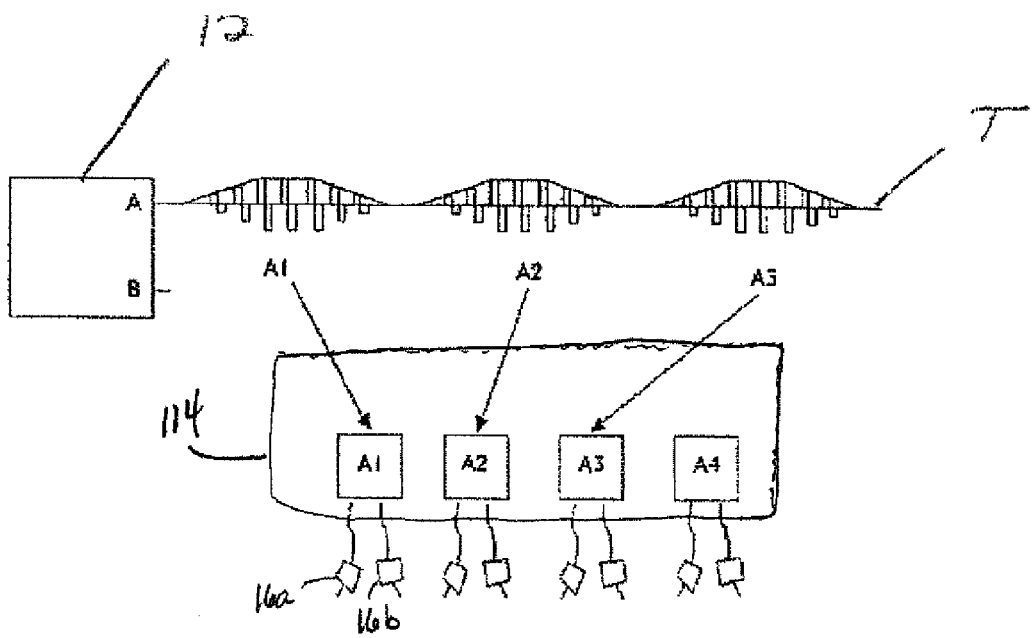
FIG. 9b illustrates the second mode of operation of the system in accordance with another embodiment of a stimulation node.

In channel phasing mode, the unit 10 may activate a selected virtual channel (A1, A2, or A3) while other channels (e.g., A4) are inactive. The unit 12 may then be used to output a traditional stimulation pulse train T. The pulses are delivered by only the electrodes 16a, 16b associated with the active virtual channel. This mode of operation is shown schematically in FIG. 9a. FIG. 9b illustrates a similar use of channel phasing mode in which a plurality of virtual channels (A1-A4) are associated with a single node 114. Pulse sharing mode and channel phasing mode may be used in combination such that the stimulation unit 12 essentially has an unlimited number of channels for a given transmission line 18.

Figure 10:
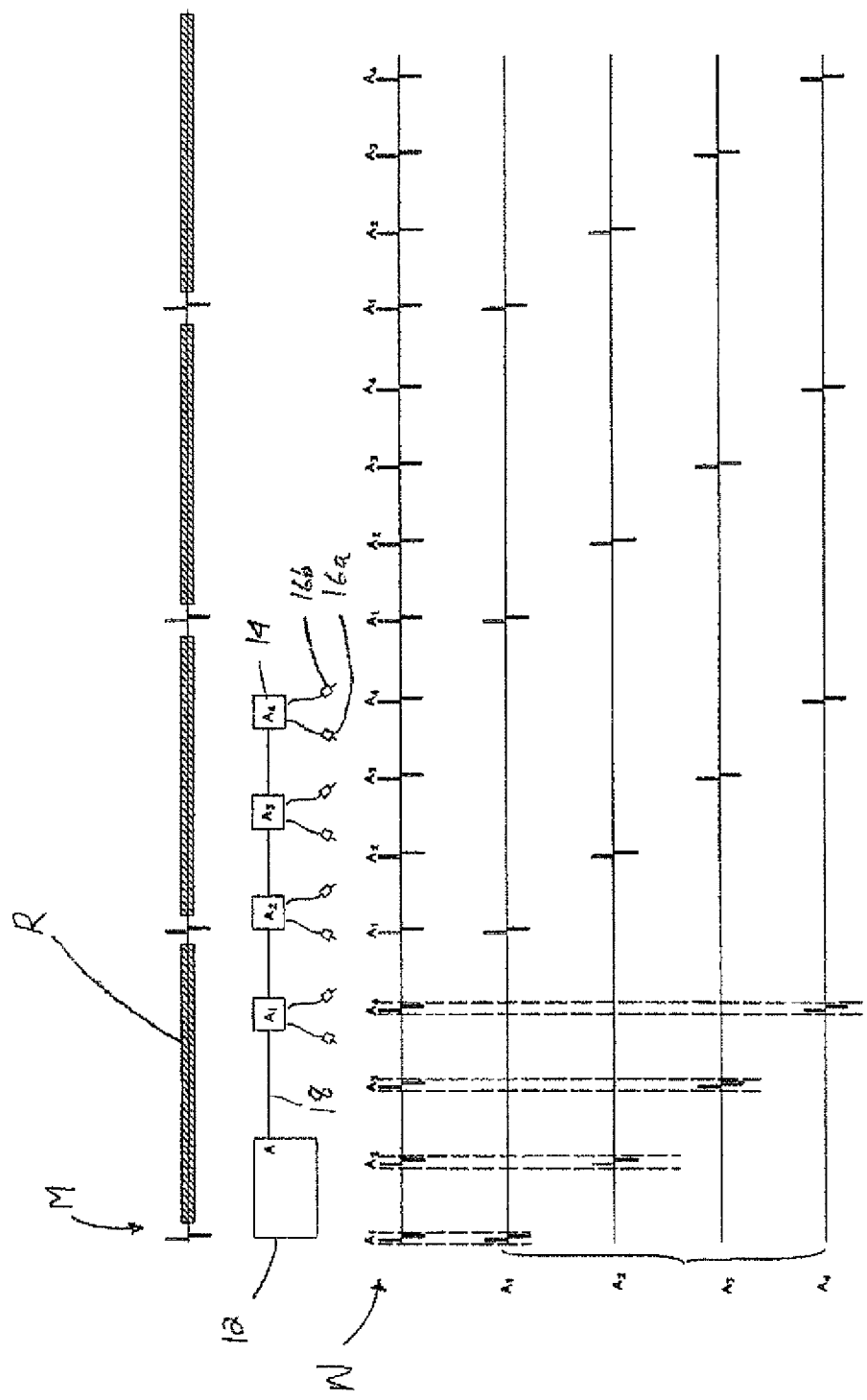
FIG. 10 is a diagram illustrating the nature of the improvement in efficiency that may be achieved using the disclosed system.

As can be best understood with reference to FIG. 10, use of these aspects of the system 10 together (which is optional) may provide several advantages. At the top of this figure, a traditional electrical stimulation pulse train M to a single electrode pair is shown. Stimulation pulses are infinitesimally small compared to the inter-pulse interval (e.g., less than or equal to 1000 µs active per every period greater than or equal to 20,000 µs). The shaded region R indicates the unused potential of the stimulation device as it waits to deliver the next pulse. With the present system 10, the stimulation unit 10 may output the interlaced pulse train N as shown, which includes pulses for virtual channels A1-A4. All connected stimulation nodes 14 receive the interlaced pulse train N and either output the pulses to the connected electrode pair 16a, 16b or block pulses intended for other nodes/virtual channels.

Figure 11A:
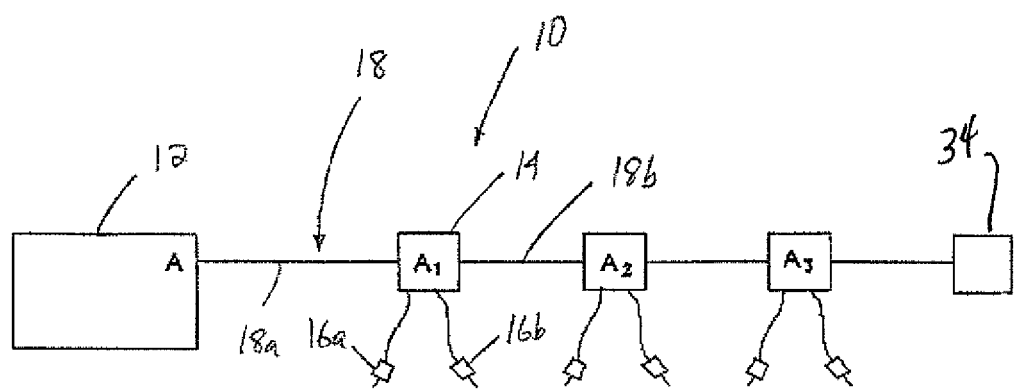
FIGS. 11a and 11b are diagrams of an embodiment of the system including a sensing module.
Figure 11B:
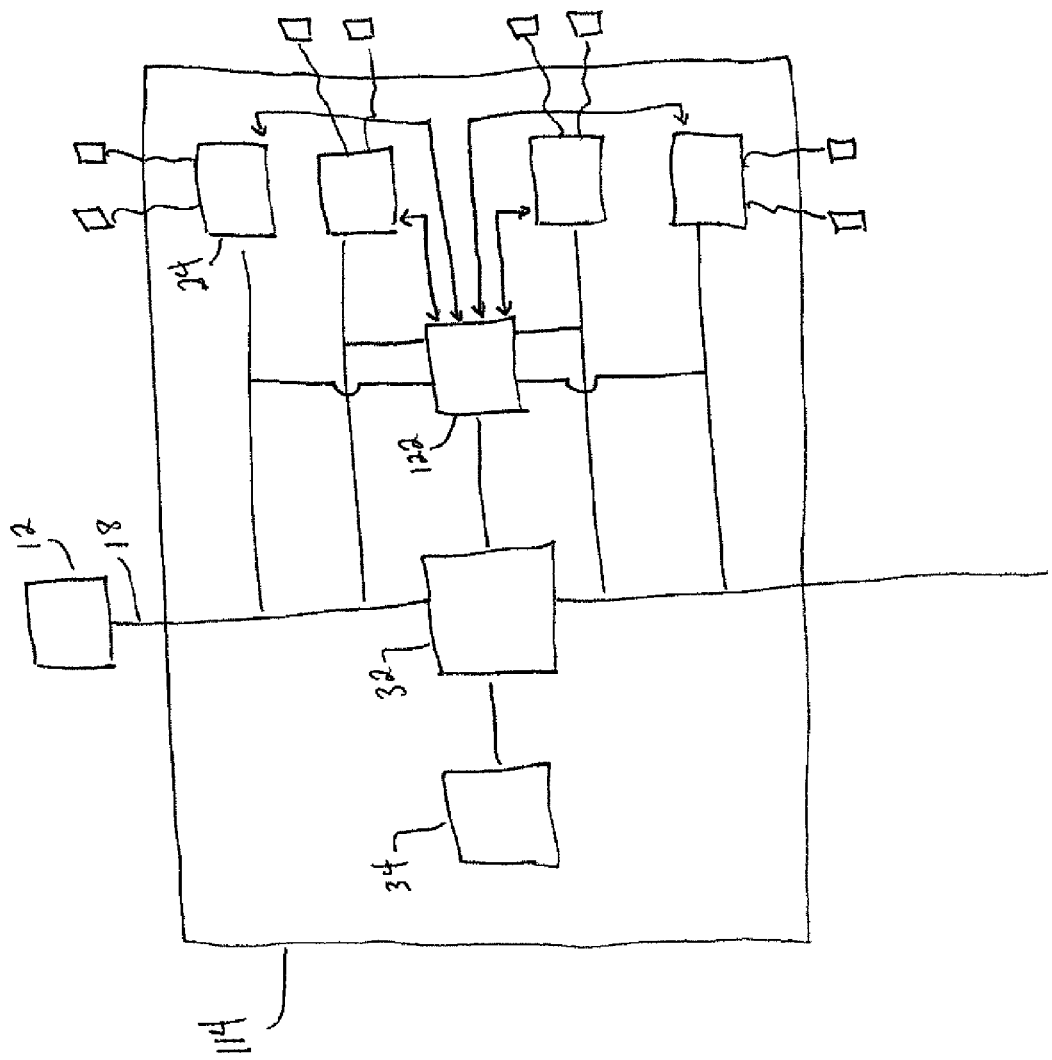

In a further embodiment as shown in FIGS. 11a and 11b, the system 10 may include one or more sensors 34. Each sensor 34 may comprise a sensing module incorporating any type of sensing device (such as, for example, an accelerometer) adapted to sense a condition (such as, for example, a position of a portion of the subject's body in space, speed and/or direction of motion of a subject's body part, a position of an electrode on the subject's body, or any other relevant information about the environment of an exercise). The information may be obtained from any number of internal or external devices, such as transducers.

The sensor 34 may be arranged in communication with the stimulation unit 12. For example, the sensor 34 may be connected directly to the transmission line 18 for delivering the sensed information to the stimulation unit 12 or any node 14, 114 within the system 10. The sensor 34 may be independent of any node 14, such as in the embodiment illustrated in FIG. 11*a*. Additionally, the sensor 34 may include a housing with one or more ports for connecting to the system and/or an instrument. Accordingly, the sensing module may be connected with the stimulation unit 12 alone, or in combination with one or more nodes 14 in a daisy-chain or star connection pattern.

Alternatively, the sensor 34 may be incorporated within a node 14, 114 such as is illustrated in FIG. 11*b*. In such an embodiment, the sensor 34 may connect directly to the transmission line, or may connect to the bus controller 32 for coordination of signal transmitted to and from the stimulation unit 12. The use of a sensor 34 in conjunction with one or more nodes 14, 114 allows for feedback and/or control within an exercise.

Figure 12:
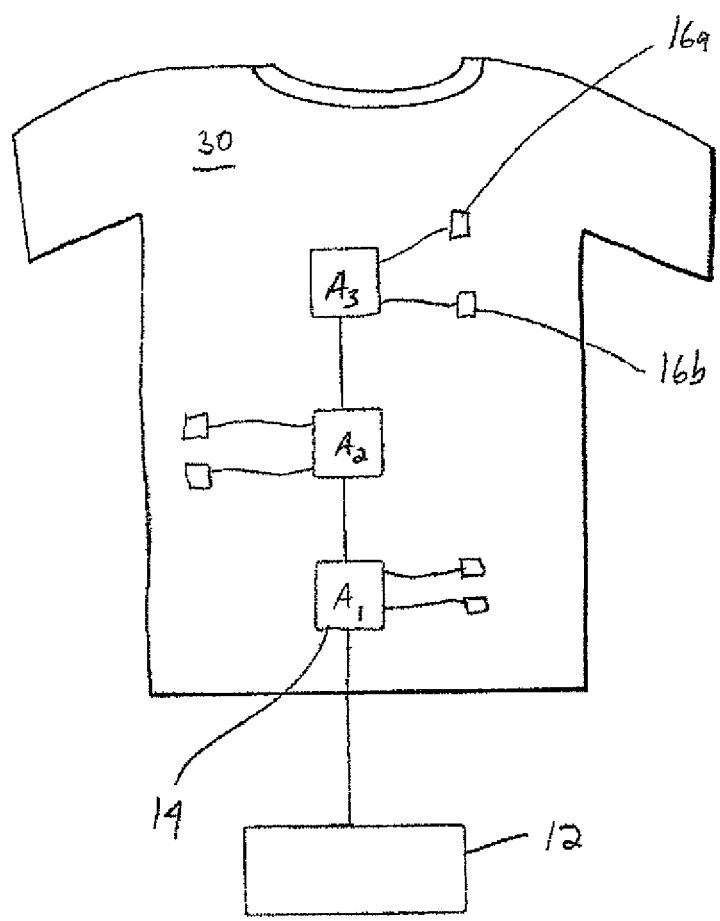
FIG. 12 is a schematic diagram of a stimulation garment that may be used in connection with the disclosed system.

The modular nature of the system 10 allows for selected components to be provided as a kit. For example, the kit may comprise a plurality of nodes 14, 114 and electrode pairs 16*a*, 16*b*, both adapted for connecting to the associated transmission line 18, 19. Additionally, one or more sensing modules 34 may be provided, either internal to a node or within an independent housing. The kit may be provided for use by product developers for use in a particular stimulation application. The components of the system 10 or the kit could also be incorporated into a stimulation garment 30 (shown as a shirt in FIG. 12 as one example, but the garment may also comprise a sleeve, band, pant, or the like, depending on the particular need of the subject).

The stimulation unit 12 may be programmed to provide the stimulation patterns desired for each electrode or group of electrodes to meet the individual needs of the patient. This programming may be done, for example, by using a software application for designing a particular stimulation regimen, including the ability to program the different virtual channels simultaneously (see FIG. 13, a screen shot from an application for designing stimulation regimens; FIG. 14, which is a pattern generator application; and FIG. 15, which is a program for designing the display output on a stimulation unit 12). Alternatively or additionally, pre-programmed stimulation paradigms may be provided, and at power-up the stimulation unit 12 may evaluate the nodes 14, 114 and automatically bypass those not in use. In this case, the array size would be easily scalable by the end user (a physical therapist or even a patient) by simply adding or removing nodes to the particular stimulation channel(s).

As should also be appreciated, the modular nature of the nodes 14, 114 allows for their positioning in an array that may be distributed among different portions of the subject's body, such as with several different muscle groups. For example, different nodes 14 may be associated with the subject's quadriceps, gluteals, and hamstrings. Alternatively or additionally, different electrode pairs operating on different virtual channels associated with a single node 114 may be associated with different portions of the body or muscle groups. In this manner, a complete stimulation solution may be provided using a single stimulation channel. The nodes 14, 114 need not be limited to a particular body part or region of the body, but may extend over multiple body parts (e.g., the chest, shoulder, and arm; the back or abdomen and legs, etc.).

The use of the modular system is not limited to use with a single patient or exercise device. For example, a single stimulation unit 12 may utilize a single channel to output an interlaced, multiple pulse stimulation signal to a plurality of patients, as illustrated in FIG. 16*a*. Similarly, a single stimulation unit 12 may be used to simultaneously stimulate subjects performing different exercises, such as those on different machines (FIG. 16*b*). Any node 14, 114 used in such a configuration may be adapted to identify itself to the stimulation unit 12, such that the node may only be used in association with the machine, patient, or body part for which it is intended. For example, a node with virtual channels intended for use with a treadmill would be adapted to identify itself to the stimulation unit 12 such that it cannot be used with an exercise bike.

Each stimulation pulse may be independent from every other pulse, and therefore may be concurrently transmitted to a different virtual channel, regardless of the location of the electrodes associated with each virtual channel. This allows for a single-channel pulse train T to simultaneously stimulate one patient according to one programmed exercise and another patient according to the same or a different programmed exercise.

To further facilitate the portability of the system 10 and concomitant ease of use, the stimulation unit 12 preferably comprises a portable, hand-held battery operated device. For example, the unit 12 may take the form of the CK200 device available from customKYnetics, Inc. of Versailles, Ky. Certain features of this unit 12 are described in U.S. patent application Ser. Nos. 12/164,554 and 60/937,633, the disclosures of which are incorporated herein by reference.

The foregoing descriptions of various embodiments of the invention are provided for purposes of illustration and not intended to be exhaustive or limiting. Modifications or variations are also possible in light of the above teachings. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. An apparatus for providing electrical stimulation to at least one subject using at least one transmission line and a plurality of pairs of electrodes, comprising:
    a stimulation unit for producing a single-channel interlaced output signal comprising a plurality of stimulation pulses, wherein said stimulation pulses are configured for selective delivery to the subject via at least one pair of electrodes.

2. The apparatus of claim 1, wherein at least one first stimulation pulse is configured to stimulate a first subject, and wherein at least one second stimulation pulse is configured to stimulate a second subject.

3. The apparatus of claim 1, further including at least one node for selecting a first stimulation pulse configured for delivery to a first pair of electrodes associated with the node.

4. The apparatus of claim 3, wherein the node is further configured for independently selecting a second stimulation pulse which is configured for delivery to a second pair of electrodes associated with the node.

5. The apparatus of claim 1, further including a plurality of nodes, each node adapted for selecting at least one stimulation pulse configured for at least one pair of electrodes associated with said node.

6. The apparatus of claim 1, wherein the stimulation unit is adapted for simultaneous use with a first piece of exercise equipment and a second piece of exercise equipment.

7. The apparatus of claim 1, wherein the stimulation unit is adapted for simultaneous use with a first subject and a second subject.

8. The apparatus of claim 1, wherein the stimulation unit is adapted for simultaneously stimulating a first portion of the subject's body using at least one first node associated with a first pair of electrodes and a second portion of the subject's body using at least one second node associated with a second pair of electrodes.

9. The apparatus of claim 1, wherein the stimulation unit is adapted for simultaneously stimulating the subject using at least one first node associated with at least two pairs of electrodes, each for stimulating a different portion of the subject's body.

10. The apparatus of claim 1, wherein the stimulation unit includes a plurality of ports, each for delivering the single-channel interlaced output signal.

11. An apparatus for providing an electrical stimulation in the form of a plurality of interlaced stimulation pulses through at least one transmission line, wherein a first stimulation pulse is intended for a first pair of electrodes for delivering said stimulation pulse to an external skin surface of a subject, said apparatus comprising:
    at least one node adapted to connect to the transmission line for receiving the plurality of stimulation pulses, said node adapted for selecting and delivering a first stimulation pulse configured for the first pair of electrodes.

12. The apparatus of claim 11, wherein the node includes a first connector for connecting to the first pair of electrodes.

13. The apparatus of claim 11, wherein the node includes a plurality of connectors, each for connecting to one of a plurality of pairs of electrodes.

14. The apparatus of claim 11, wherein the node is further adapted for selecting and delivering a second stimulation pulse configured for a second pair of electrodes associated with the node.

15. The apparatus of claim 11, further including a sensor for sensing a condition of the subject and communicating the condition to the stimulation unit.

16. The apparatus of claim 15, wherein the sensor is connected to the node.

17. The apparatus of claim 11, further including a stimulation unit for generating the output stimulation via a single channel.

18. The apparatus of claim 17, wherein the stimulation unit further includes a plurality of ports for distributing the single-channel output stimulation to the at least one node.

19. An apparatus for stimulating a subject via at least one first pair of electrodes, comprising:
    a stimulation unit for producing a single-channel interlaced output signal comprising a plurality of stimulation pulses, wherein at least one first pulse is configured for the first pair of electrodes; and
    at least one node for receiving the plurality of stimulation pulses and for selecting and delivering the first pulse to the first pair of electrodes.

20. The apparatus of claim 19, further including a sensor for sensing a condition of the subject and for communicating information regarding the condition to the stimulation unit.

21. An exercise device for use with the apparatus of claim 19.

22. The apparatus of claim 11, wherein the node includes a pulse selection circuit for monitoring the plurality of stimulation pulses on the transmission line on a pulse-by-pulse basis.

23. The apparatus of claim 22, wherein the node further includes a pulse gating circuit operable between a pass through mode for allowing a stimulation pulse to pass to the electrodes and a blocking mode for blocking a stimulation pulse from passing to the electrodes, and wherein the pulse selection circuit switches the pulse gating circuit between the pass through mode and the blocking mode based on a characteristic of a given stimulation pulse.

* * * * *

UNITED STATES PATENT AND TRADEMARK OFFICE
CERTIFICATE OF CORRECTION

| | | |
|---|---|---|
| PATENT NO. | : 8,676,333 B1 | Page 1 of 1 |
| APPLICATION NO. | : 13/621453 | |
| DATED | : March 18, 2014 | |
| INVENTOR(S) | : Eric C. Hartman et al. | |

It is certified that error appears in the above-identified patent and that said Letters Patent is hereby corrected as shown below:

On the Title Page

Item (71) and (72) should read,

Natalie A. Hatfield

Signed and Sealed this
Third Day of March, 2015

Michelle K. Lee
*Deputy Director of the United States Patent and Trademark Office*